(12) United States Patent
Haecker et al.

(10) Patent No.: US 9,757,503 B2
(45) Date of Patent: Sep. 12, 2017

(54) DEVICE AND METHOD FOR MONITORING THE CONNECTION OF A BLOOD TREATMENT UNIT TO THE FLUID SYSTEM OF AN EXTRACORPOREAL BLOOD TREATMENT APPARATUS

(75) Inventors: Juergen Haecker, Neu-Anspach (DE); Soeren Gronau, Nauheim (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 744 days.

(21) Appl. No.: 13/640,881

(22) PCT Filed: Apr. 14, 2011

(86) PCT No.: PCT/EP2011/001891
§ 371 (c)(1),
(2), (4) Date: Oct. 12, 2012

(87) PCT Pub. No.: WO2011/128098
PCT Pub. Date: Oct. 20, 2011

(65) Prior Publication Data
US 2013/0026098 A1 Jan. 31, 2013

(30) Foreign Application Priority Data

Apr. 14, 2010 (DE) .......................... 10 2010 015 003
Jul. 23, 2010 (DE) .......................... 10 2010 032 154

(51) Int. Cl.
*A61M 1/16* (2006.01)
*G01L 7/00* (2006.01)

(52) U.S. Cl.
CPC ............ *A61M 1/16* (2013.01); *A61M 2205/15* (2013.01); *A61M 2205/276* (2013.01); *A61M 2205/3331* (2013.01)

(58) Field of Classification Search
CPC ................ A61M 1/16; A61M 2205/15; A61M 2205/276; A61M 2205/3331
(Continued)

(56) References Cited

U.S. PATENT DOCUMENTS

2002/0121471 A1 9/2002 Pedrazzi
2003/0136181 A1* 7/2003 Balschat et al. ........... 73/40.5 R
(Continued)

FOREIGN PATENT DOCUMENTS

| DE | 102 01 109 C1 | 1/2003 |
| EP | 1 078 642 A2 | 2/2001 |
| WO | 2005/107833 A1 | 11/2005 |

OTHER PUBLICATIONS

PCT International Search Report from PCT/EP2011/001891, mailed on May 31, 2012.
(Continued)

*Primary Examiner* — Dirk Bass
(74) *Attorney, Agent, or Firm* — Kilyk & Bowersox, P.L.L.C.

(57) ABSTRACT

A device and method for monitoring the connection of a blood treatment unit to a fluid system of an extracorporeal blood treatment apparatus are described, in which the blood treatment unit includes an inlet and an outlet for connection to the fluid system and the fluid system includes a line system with a first line segment connected to the inlet and a second line segment connected to the outlet. An extracorporeal blood treatment apparatus includes a device for monitoring the connection of the blood treatment unit to the fluid system. The device and method for monitoring the connection of the blood treatment unit to the fluid system is based on measurement of pressure in the fluid system of the blood treatment apparatus. Solely on the basis of the pressure measurement, it is ascertained whether the connection
(Continued)

of the blood treatment unit to the fluid system is correct or incorrect.

20 Claims, 7 Drawing Sheets

(58) Field of Classification Search
USPC .............. 210/143, 321.72, 646, 97; 73/700
See application file for complete search history.

(56) References Cited

U.S. PATENT DOCUMENTS

| | | |
|---|---|---|
| 2005/0145549 A1 | 7/2005 | Jonsson et al. |
| 2006/0079827 A1 | 4/2006 | Jensen et al. |
| 2012/0318740 A1* | 12/2012 | Ekdahl et al. ...... A61M 1/3626 210/646 |

OTHER PUBLICATIONS

International Preliminary Report on Patentability from PCT/EP2011/001891, mailed on Oct. 16, 2012.

* cited by examiner

DEVICE AND METHOD FOR MONITORING THE CONNECTION OF A BLOOD TREATMENT UNIT TO THE FLUID SYSTEM OF AN EXTRACORPOREAL BLOOD TREATMENT APPARATUS

CROSS REFERENCE TO RELATED APPLICATIONS

The present application is the national stage entry of International Patent Application No. PCT/EP2011/001891, filed on Apr. 14, 2011, which claims priority to Application No. DE 10 2010 015 003.7, filed in the Federal Republic of Germany on Apr. 14, 2010, and Application No. DE 10 2010 032 154.0, filed in the Federal Republic of Germany on Jul. 23, 2010.

FIELD OF INVENTION

The present invention relates to a device and a method for monitoring the connection of a blood treatment unit to the fluid system of an extracorporeal blood treatment apparatus, in which the blood treatment unit comprises an inlet and an outlet for connection to the fluid system and the fluid system comprises a line system with a first line segment which is connected to the inlet and a second line segment which is connected to the outlet of the blood treatment unit. Moreover, the present invention relates to an extracorporeal blood treatment apparatus with a device for monitoring the connection of the blood treatment unit to the fluid system of the blood treatment apparatus, in particular the dialysing fluid system of the blood treatment apparatus.

BACKGROUND INFORMATION

Various kinds of blood treatment apparatuses are known. The known blood treatment apparatuses include, for example, the apparatuses for haemodialysis, haemofiltration and haemodiafiltration. During the blood treatment, the patient's blood flows in an extracorporeal blood circuit through a blood treatment unit. In the case of the apparatuses for haemodialysis, haemofiltration and haemodiafiltration, the blood treatment unit is a dialyser or filter, which is separated by a semi-permeable membrane into a blood chamber and a dialysing fluid chamber. During the blood treatment, the blood flows through the blood chamber, whilst the dialysing fluid flows through the dialysing fluid chamber. An effective blood treatment requires that blood and dialysing fluid flow in opposite directions along the membrane of the dialyser or filter. In the case of a flow in the same direction, the blood treatment is less effective.

The dialyser or filter is an interchangeable unit, which is connected to the fluid system of the blood treatment apparatus. The fluid system of the known blood treatment apparatuses comprises a line system with a first and a second line segment for the connection of the blood treatment unit. For the connection of the dialyser or filter to the fluid system, the first line segment is connected to the inlet of the dialysing fluid chamber and the second line segment is connected to the outlet of the dialysing fluid chamber of the dialyser. The connection of the dialyser takes place with known connection pieces, which include the known Hansen couplings.

The manufacturers of dialysers and blood treatment apparatuses provide a colour coding of the inlet and outlet of the dialyser and of the Hansen couplings to be connected to the inlet and outlet, in order to make it easier for the user to make the correct connection according to the counter-flow principle. This colour coding, however, is not uniform with all manufacturers. There is therefore the risk of the connections being confused, which will be referred to below as an incorrect connection. The effect of this is that the dialyser is not operated with a counter-flow. Consequently, the effectiveness of the treatment for the patient is inadequate. This is problematic, inasmuch as an incorrect connection of the dialyser may possibly remain unnoticed. In principle, therefore, there is the risk of the patient being treated with inadequate efficiency over a long period.

SUMMARY

An object of the present invention is to provide a device and a method which increase reliability in dialysis.

The device according to the present invention and the method according to the present invention for monitoring the connection of a blood treatment unit to the fluid system of an extracorporeal blood treatment apparatus are based on the measurement of at least one pressure in the fluid system of the blood treatment apparatus. Solely on the basis of the at least one pressure measurement, it is ascertained whether the connection of the blood treatment unit to the fluid system is correct or incorrect.

The monitoring device according to the present invention provides a device for measuring the pressure in the first and/or second line segment of the line system of the blood treatment apparatus. In principle, it is possible to measure the pressure only in one of the two line segments in order to monitor the correct connection of the blood treatment unit to only one of the two line segments. If the one line segment is incorrectly connected, the other line segment must also be incorrectly connected.

It has been shown that the static pressure conditions of the line segments filled completely with fluid change with the height position of the line segments in space, while the dialyser is not filled with fluid. This is due to the fact that, in the case of the known blood treatment apparatuses, the blood treatment unit and the line segments of the line system to be connected to the latter lie at different heights.

In general, the inlet and outlet of both chambers of the blood treatment unit do not lie in a common horizontal plane, but rather one above the other. With the known blood treatment apparatuses, the inlet of the dialysing fluid chamber of the dialyser, depending on the type of dialyser, lies either above or below the outlet of the dialysing fluid chamber of the dialyser. If the dialyser is not correctly connected, different pressure conditions from those with a correct connection result. This change in the pressure conditions is the basis for the detection of an incorrect connection.

With the monitoring device according to the present invention and the monitoring method according to the present invention, it is not the integrity, in particular tightness, of the connections or the line system that is checked, but rather a check is made to establish whether the blood treatment unit is correctly connected to the fluid system of the blood treatment apparatus.

In a preferred exemplary embodiment of the present invention, the pressure is monitored not only in one of the two line segments, but in both line segments, in order to work out the difference between the pressure measured in the first line segment and that measured in the second line segment. The monitoring of the pressure difference has the advantage that the arrangement of the dialyser or filter at different heights does not lead to different measurement results, since it is not an absolute magnitude, but only a relative measured variable that is evaluated. The connection of the blood treatment unit can thus be monitored with a high degree of reliability even when the blood treatment unit is to be inserted at different heights into the holding fixtures provided on the blood treatment apparatuses.

A particularly preferred exemplary embodiment makes provision such that the pressure difference between the pressure in the first line segment and the pressure in the second line segment is compared with a preset threshold value. If the pressure difference is greater than the preset threshold value, it is concluded that there is a correct connection of the blood treatment unit. If, on the other hand, the pressure difference is less than the preset threshold value, it is concluded that there is an incorrect connection. This requires, however, that the inlet of the dialyser lies above the outlet. In the case where the inlet lies below the outlet, it is concluded that there is a correct connection of the blood treatment unit if the pressure difference is less than the preset threshold value.

In the case where the connection of the blood treatment unit is incorrect, an optical, acoustic and/or tactile alarm is preferably emitted. Moreover, the performance of the blood treatment is preferably prevented, so that the performance of the blood treatment is possible only with a correct connection of the blood treatment unit.

The monitoring device according to the present invention and the monitoring method according to the present invention can be used with the known blood treatment apparatuses without major modification measures being required for this. The device for measuring the pressure in the two line segments of the line system is in any case present in the known blood treatment apparatuses. Shut-off elements are also present in both line segments in the known blood treatment apparatuses. The check does however require that the lines on the dialysate side are completely filled with fluid, but that the dialyser is not filled with fluid. Ambient pressure therefore predominates at the end of the dialyser couplings, in particular Hansen couplings, present in the known blood treatment apparatuses.

The check on the connection of the blood treatment unit can take place after the obligatory rinsing procedure. However, only the line segments of the fluid system leading to the blood treatment unit and leading away from the blood treatment unit may be filled with fluid, but not the blood treatment unit, in particular the dialysing fluid chamber of the dialyser or filter. To perform the rinsing procedure, the line system of the fluid system of the blood treatment apparatus is completely filled with fluid. The recording of the pressure measurement values preferably takes place after the opening of the shut-off elements in the two line segments of the line system.

In a particularly preferred exemplary embodiment, the central control unit of the blood treatment apparatus and the evaluation unit of the monitoring device cooperate in such a way that the measuring procedure automatically proceeds after opening of the shut-off elements.

The device according to the present invention and the method according to the present invention allow not only the reliable monitoring of the connection of the blood treatment unit, but also enable complete documentation when the result of the check is stored. If the treatment is not prevented in the case of an incorrect connection of the blood treatment unit, it is also still possible after performing the treatment, when the blood treatment unit is again separated from the fluid system, to trace back whether the connection of the blood treatment unit was correct. If this was not the case, the doctor can take appropriate measures.

The exemplary embodiments described above serve only for the monitoring of the connection of the blood treatment unit. It should therefore be as straightforward as possible for the user to allocate the line segments of the line system to the appropriate connections of the blood treatment unit. This can take place in a known manner by using colour coding.

In a further preferred exemplary embodiment, it is in principle possible to dispense with allocating the line segments of the line system to the connections of the blood treatment unit by using, for example, colour coding. This exemplary embodiment provides a device for reversing the flow direction in order to reverse the flow direction in the case of an incorrect connection, i.e. if the blood treatment unit is not being operated with a counter-flow, so that the blood treatment unit is then operated with a counter-flow. In this exemplary embodiment, the evaluation unit of the monitoring device cooperates with the device for reversing the flow direction in such a way that the evaluation unit activates the device for reversing the flow direction if an incorrect connection of the blood treatment unit to the fluid system is ascertained. The correct flow direction, i.e. operation of the dialyser with a counter-flow, can thus be produced without the Hansen couplings having to be reconnected manually.

It should be noted that the device for reversing the flow direction on the dialysing fluid side has its own inventive significance. The device for reversing the flow direction can therefore be used not only with the device according to the present invention for monitoring the connection of the blood treatment unit, but also with all extracorporeal blood treatment apparatuses which, apart from the extracorporeal blood circuit, comprise a fluid system which comprises a line system with a first line segment which is connected to the inlet of a blood treatment unit, in particular to the inlet of the dialysing fluid chamber of a dialyser or filter, and comprises a second line segment which is connected to the outlet of the blood treatment unit, in particular to the outlet of the dialysing fluid chamber. The blood treatment apparatus is therefore characterised by a device for reversing the flow direction which is constituted such that, in a first position, the first line segment leads to the inlet of the blood treatment unit and the second line segment leads to the outlet of the blood treatment unit and that, in a second position, the first line segment leads to the outlet of the blood treatment unit and the second line segment leads to the inlet of the blood treatment unit when the blood treatment unit is connected to the fluid system.

Exemplary embodiments of the present invention are explained in greater detail below with reference to the accompanying drawings.

DETAILED DESCRIPTION

Figure 1:
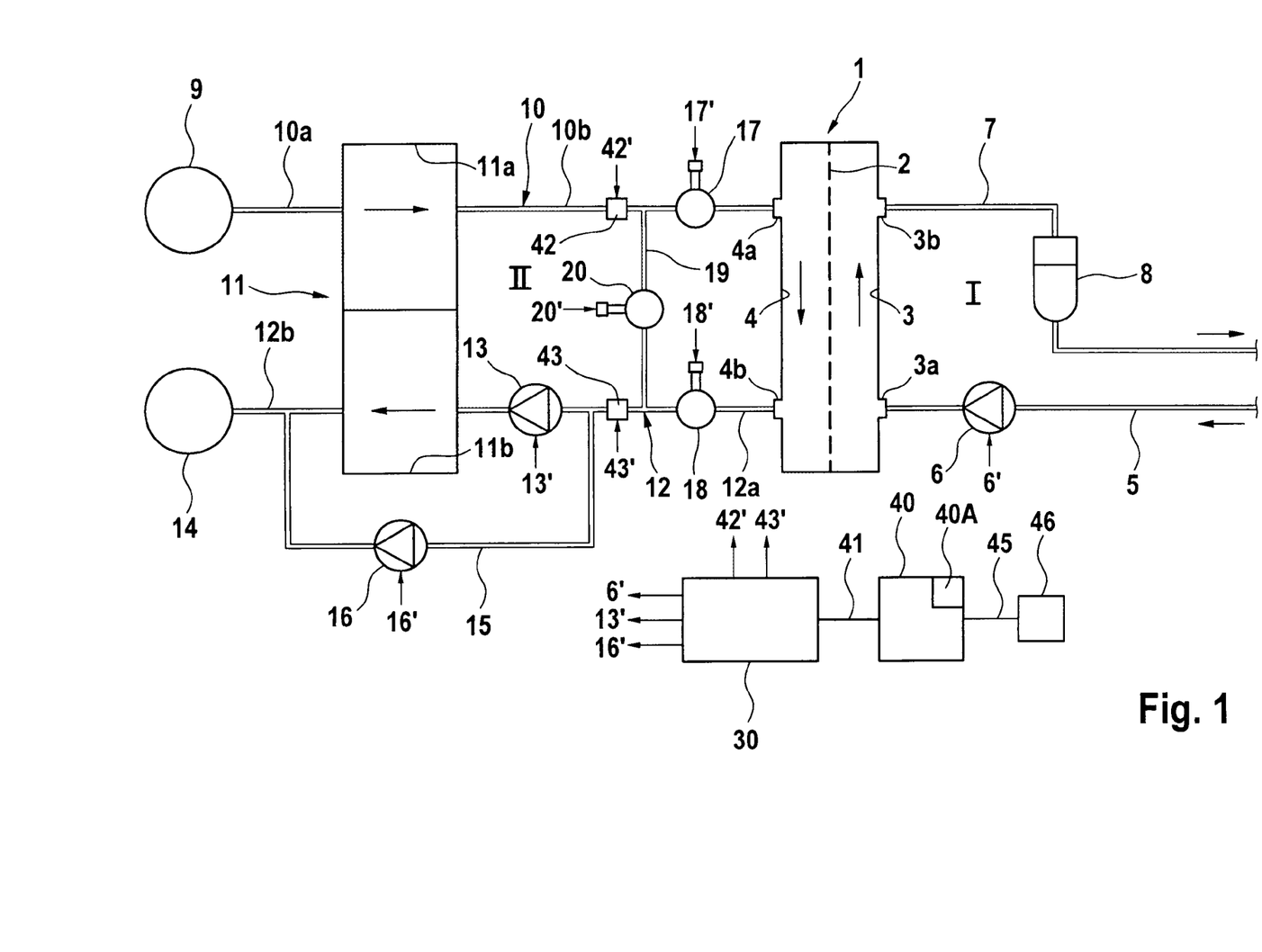
FIG. 1 shows, in a very simplified schematic representation, the main components of a blood treatment apparatus.

FIG. 1 shows, in a very simplified schematic representation, the main components of a blood treatment apparatus. In the present exemplary embodiment, the blood treatment apparatus is a haemodialysis apparatus, which comprises a dialyser 1 which is separated by a semi-permeable membrane 2 into a blood chamber 3 and a dialysing fluid chamber 4. Inlet 3a of the blood chamber is connected to one end of arterial blood line 5, into which a blood pump 6 is incorporated, whilst outlet 3b of the blood chamber is connected to one end of venous blood line 7, into which a drip chamber 8 is incorporated. Located at the other ends of arterial and venous blood lines 5, 7 are the arterial and venous cannulas (not shown) for connection to the patient. This part of the blood treatment apparatus represents extracorporeal blood circuit I.

The method according to the present invention and the device according to the present invention are described below using the exemplary haemodialysis apparatus. The method according to the present invention and the device according to the present invention can however also be used in the same way with a haemodiafiltration apparatus, since the kind of dialysis apparatus does not have any influence on the method according to the present invention and the device according to the present invention.

The fluid system of the blood treatment apparatus comprises an arrangement 9 for making available fresh dialysing fluid, which is connected via a first segment 10a of a dialysing fluid supply line 10 to the inlet of a chamber half 11a of a balancing arrangement 11. Second segment 10b of dialysing fluid supply line 10 connects the outlet of the one balancing chamber half 11 a to inlet 4a of dialysing fluid chamber 4. Outlet 4b of dialysing fluid chamber 4 is connected via first segment 12a of dialysing fluid discharge line 12 to the inlet of the other balancing chamber half 11b of balancing arrangement 11. A dialysing fluid pump 13 is incorporated into first section 12a of dialysing fluid discharge line 12. The outlet of the other balancing chamber half 11b is connected via second segment 12b of dialysing fluid discharge line 12 to a drain 14. Branching off from dialysing fluid discharge line 12 upstream of dialysing fluid pump 13 is an ultrafiltrate line 15 which also leads to drain 14. An ultrafiltration pump 16 is incorporated into ultrafiltrate line 15.

During the blood treatment, the patient's blood flows through blood chamber 3 and the dialysing fluid flows through dialysing fluid chamber 4 of dialyser 1. Blood and dialysing fluid flow along membrane 2 of dialyser 1 in opposite directions. This requires a correct connection of blood treatment unit 1 to fluid system II and extracorporeal blood circuit I.

The blood treatment apparatus comprises a central control unit 30, which is connected via control lines 6', 13', 16' to blood pump 6, dialysing fluid pump 13 and ultrafiltration pump 16.

Dialysing fluid supply line and dialysing fluid discharge line 10, 12 form a part of the line system of fluid system II of the blood treatment apparatus. Line segment 10b of fluid system II leading to blood treatment unit 1 and line segment 12a of the fluid system leading away from blood treatment unit 1 are hose lines which are connected to inlet and outlet 4a, 4b of dialysing fluid chamber 4 of dialyser 1. This part of the fluid system is described in greater detail below by reference to FIGS. 2A and 2B.

For the separation of blood treatment unit 1 from fluid system II, a first shut-off element 17 is located in dialysing fluid supply line 10 and a second shut-off element 18 is located in dialysing fluid discharge line 12. Branching off from dialysing fluid supply line 10 upstream of first shut-off element 17 is a bypass line 19, which leads to dialysing fluid discharge line 12 downstream of second shut-off element 18. A third shut-off element 20 is incorporated into bypass line 19. Shut-off elements 17, 18, 20 are preferably electromagnetically actuated shut-off elements, which are controlled by central control unit 30 via control lines 17', 18', 20'.

The device for monitoring the correct connection of blood treatment unit 1 to fluid system II of the blood treatment apparatus is described in detail below.

The monitoring device can form an independent unit, but can also be a component part of the blood treatment apparatus. Since the known blood treatment apparatuses already comprise components which the monitoring device also makes use of, the monitoring device is preferably a component part of the blood treatment apparatus.

The monitoring device comprises a computing and evaluation unit 40, which is represented in FIG. 1. Computing and evaluation unit 40 is connected via a data line 41 to central control unit 30 of the blood treatment apparatus. Computing and evaluation unit 40 can however also be a component of central control unit 30.

The monitoring device comprises a first pressure sensor 42, which measures the pressure in dialysing fluid supply line 10 upstream of first shut-off element 17. Furthermore, evaluation unit 40 comprises a second pressure sensor 43, which measures the pressure in dialysing fluid discharge line 12 downstream of second shut-off element 18. Both pressure sensors 42, 43 are connected via data lines 42', 43' to computing and evaluation unit 40, so that computing and evaluation unit 40 can evaluate the measured values of the pressure sensors.

Figure 2A:
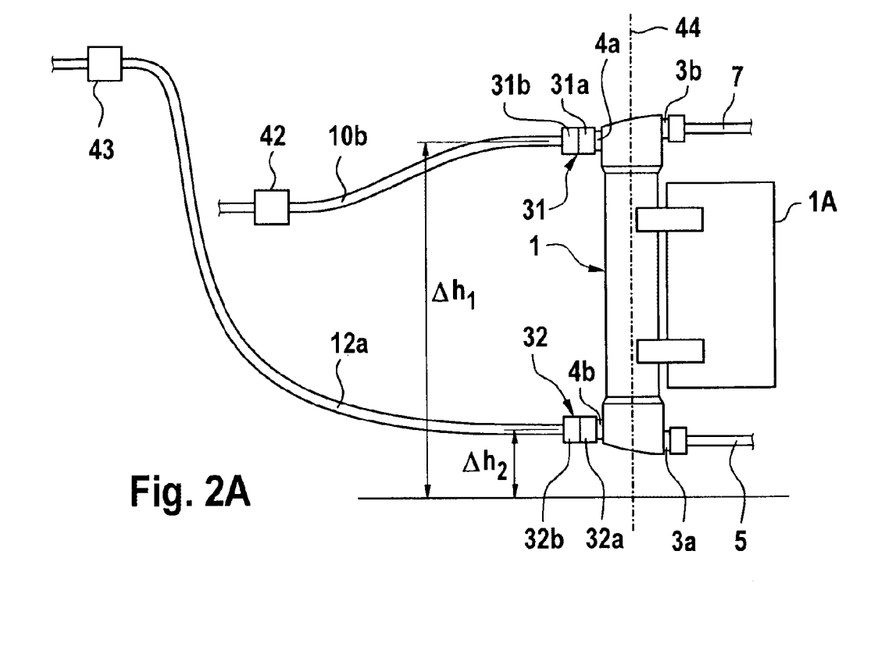
FIG. 2A shows a schematic representation of the arrangement of the blood treatment unit and the line segments of the line system of the fluid system of the blood treatment apparatus correctly connected to the blood treatment unit.
Figure 2B:
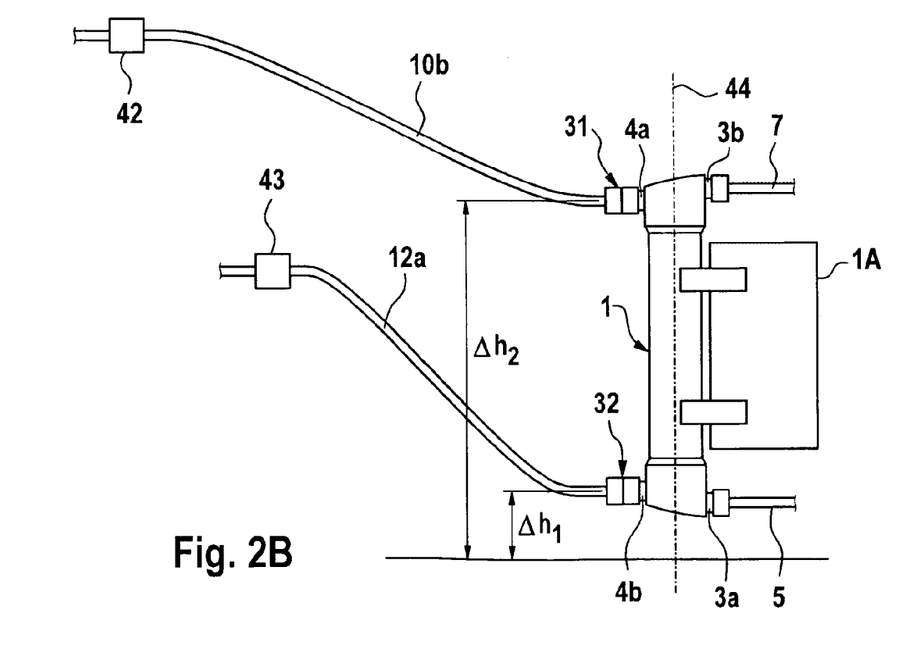
FIG. 2B shows the line segments of the line system incorrectly connected to the blood treatment unit.

FIGS. 2A and 2B show the part of the fluid system of the blood treatment apparatus that comprises line segments 10b, 12a of the line system leading to blood treatment unit 1. For the sake of better clarity, the bypass line and the shut-off elements are not represented.

The blood treatment unit, in particular dialyser 1, is inserted into a holding fixture 1A of the blood treatment apparatus, said holding fixture being represented only schematically. The dialyser is disposed in holding fixture 1A in such a way that inlet and outlet 4a, 4b of the dialyser lie at different heights. In the exemplary embodiment, longitudinal axis 44 of dialyser 1 is arranged in the vertical direction, inlet 4a lying above and outlet 4b of dialysing fluid chamber 4 lying below. The height of inlet 4a and the height of outlet 4b in relation to a reference height are denoted by $\Delta h_1$ and $\Delta h_2$.

Before the blood treatment is performed, the blood treatment apparatus is rinsed and vented in a known manner. Dialysing fluid chamber 4 of dialyser 1 is not filled with fluid before the checking of the correct connection of the dialyser. The fluid system is otherwise filled with fluid. In order to be able to fill dialysing fluid supply and discharge lines 10, 12 completely with fluid, the lines can be short-circuited at the time of the rinsing, for example with a short-circuit piece (not shown). For the purpose of rinsing, shut-off elements 17 and 18 in dialysing fluid supply and discharge lines 10, 12 are opened and shut-off element 20 in bypass line 19 is closed.

Blood treatment unit 1 is now connected to line segments 10b, 12a of dialysing fluid supply and discharge lines 10, 12. For the connection of the blood treatment unit, shut-off elements 17 and 18 in dialysing fluid supply and discharge lines 10, 12 are again closed and the short-circuit piece is removed. After the connection of the blood treatment unit, shut-off elements 17 and 18 can be opened again and shut-off element 20 can be closed.

The connection of the line segments to the blood treatment unit takes place with known connection pieces 31, 32, in particular Hansen couplings. The corresponding coupling pieces of the Hansen coupling are colour-coded, for example dialyser-side coupling piece 31 a of inlet 4a and line-side coupling piece 31b of Hansen coupling 31 to be connected to the inlet are marked red, whilst dialyser-side coupling piece 32a of outlet 4b and corresponding line-side coupling piece 32b are marked blue.

After the connection of blood treatment unit 1 to fluid system II, the control unit closes shut-off element 20 in bypass line 19 and opens first and second shut-off elements 17 and 18 in supply and discharge lines 10, 12, dialysing fluid chamber 4 not being filled with fluid. After the opening of the two shut-off elements, computing and evaluation unit 40 detects, with first and second pressure sensors 42, 43, the pressure in line segment 10b of supply line 10 and in line segment 12a of discharge line 12. The pressure measurement should take place after the lapse of a short delay time, so that transient effects due to switching over the shut-off elements have died away.

Computing and evaluation unit 40 now calculates the difference between the pressure in the supply, which is measured with first pressure sensor 42, and the pressure in the discharge, which is measured with second pressure sensor 43. Computing and evaluation unit 40 compares the amount of calculated pressure difference $\Delta p$ with a preset threshold value. If the amount of the pressure difference is greater than the threshold value, computing and evaluation unit 40 ascertains a correct connection of the blood treatment unit to fluid system II. If, on the other hand, the amount of the pressure difference is less than or equal to the threshold value, the computing and evaluation unit ascertains an incorrect connection. This requires, however, that inlet 4a of dialyser 1 lies above outlet 4b. In the case where the inlet lies below the outlet, it is concluded that there is a correct connection of the blood treatment unit if the pressure difference is less than a preset threshold value. In the present exemplary embodiment, however, the inlet of the dialyser lies above the outlet.

In the case of an incorrect connection, computing and evaluation unit 40 generates a control signal which is received by central control unit 30 via data line 41. Central control unit 30 now intervenes into the machine control. This intervention can consist in the fact that the performance of the blood treatment is prevented. Evaluation and computing unit 40 is connected via a data line 45 to an alarm unit 46, which emits an optical, acoustic and/or tactile alarm in the case of an incorrect connection. For example, an error message with an indication of the cause of the error can take place on a display unit of the blood treatment apparatus, in particular on a display screen.

Figure 3A:
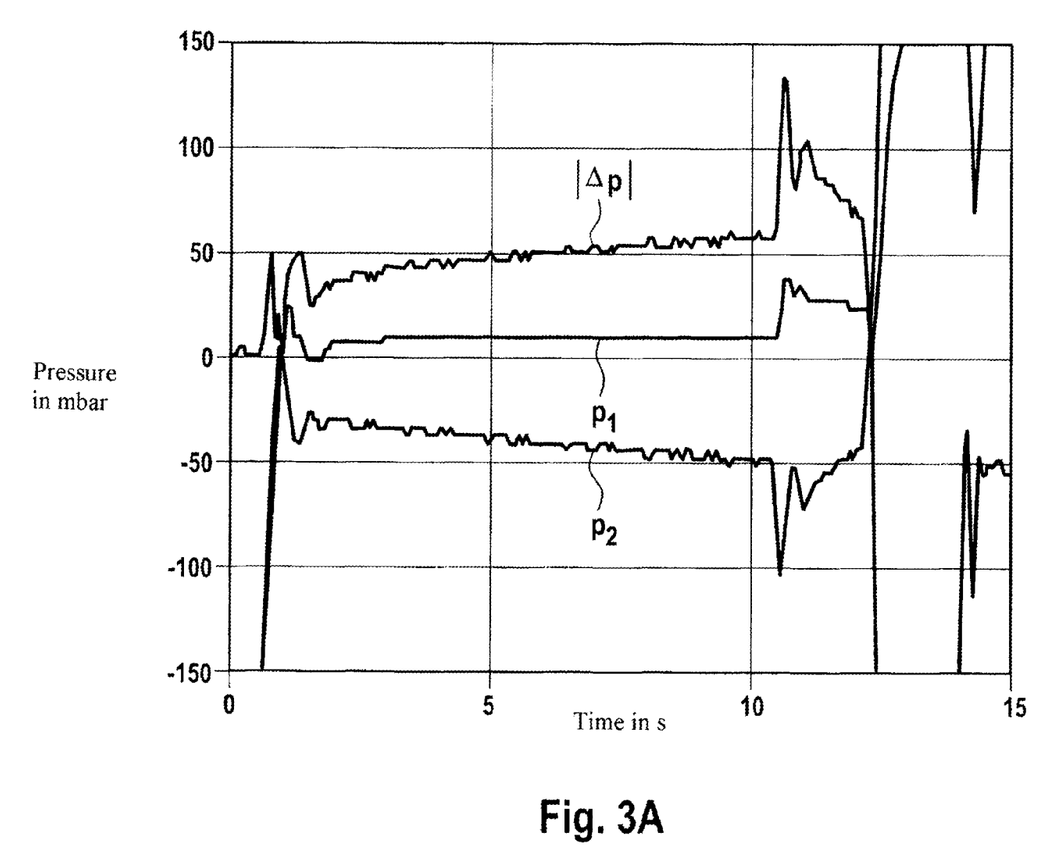
FIG. 3A shows the pressure conditions with a correct connection of the blood treatment unit.

FIG. 3A shows the pressure conditions with a correct patient connection, which is represented in FIG. 2A. It can be seen that pressure $p_1$ in the supply rises after the opening of shut-off elements 17, 18, whilst pressure $p_2$ in the discharge falls. A pressure difference $\Delta p = p_1 - p_2$ results. A single pressure measurement at a specific time after opening of the shut-off elements is in principle sufficient to determine the pressure difference. Several pressure measurements can also be carried out with sensors 42, 43 and the measured values evaluated statistically. For example, the mean value from several pressure measurements can be taken. It can be seen that the amount of pressure difference $\Delta p = p_1 - p_2$ lies between 40 and 60 mbar. The computing and evaluation unit calculates, for example, the mean value which lies at 50 mbar.

Figure 3B:
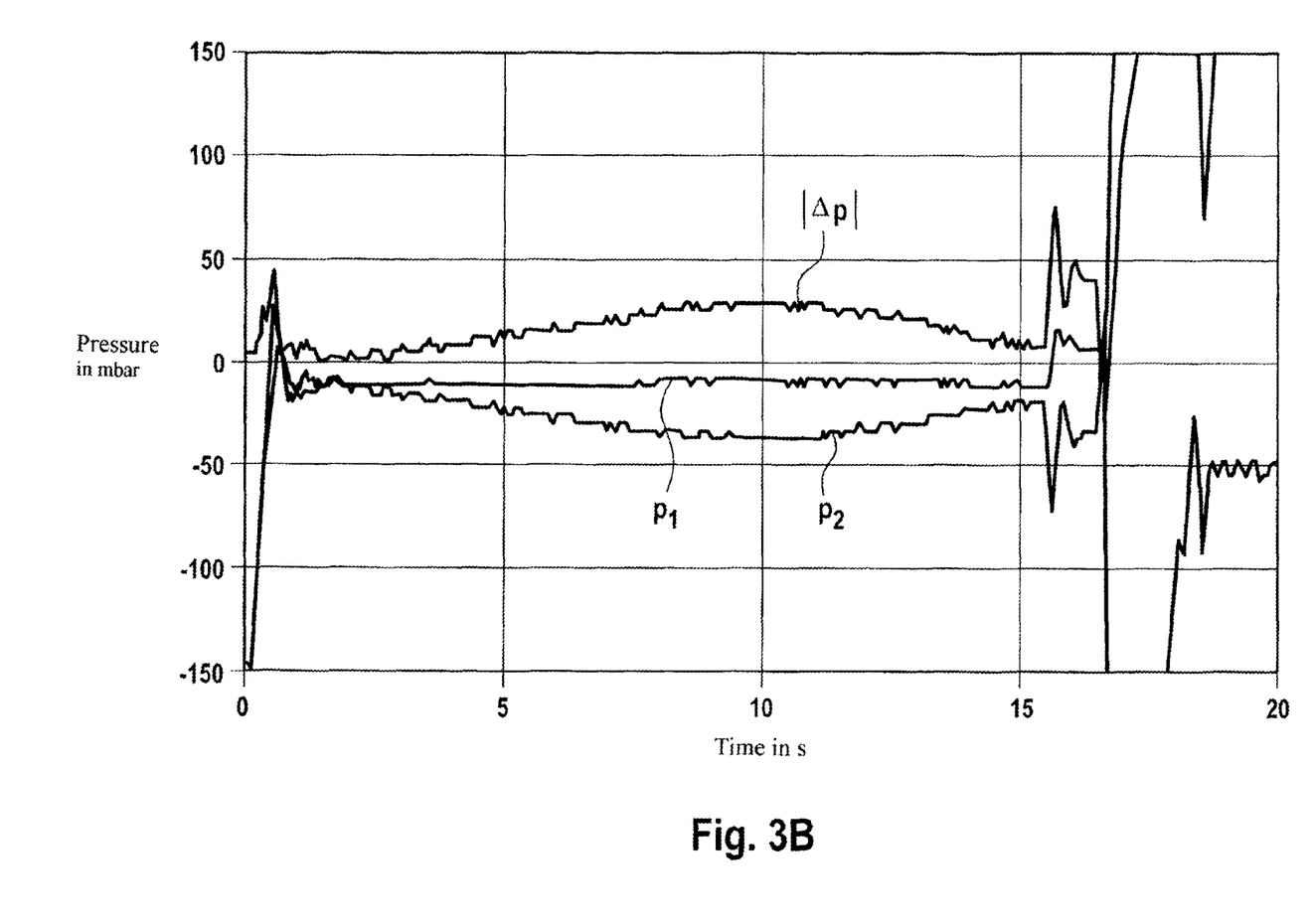
FIG. 3B shows the pressure conditions with an incorrect connection of the blood treatment unit.

FIG. 3B shows the pressure conditions with an incorrect connection (FIG. 2B). The amount of pressure difference $\Delta p = p_1 - p_2$ amounts to a maximum of 30 mbar.

In the present exemplary embodiment, the preset threshold value is 40 mbar. Computing and evaluation unit 40 compares the amount of the maximum pressure difference $\Delta p$ of 50 mbar with the preset threshold value of 40 mbar. Since the amount of pressure difference $\Delta p$ is greater than the preset threshold value, computing and evaluation unit 40 ascertains the correct connection of the blood treatment unit to the fluid system (FIGS. 2A and 3A). If, on the other hand, a value of 30 mbar is calculated for the amount of the pressure difference, computing and evaluation unit 40 ascertains an incorrect connection (FIGS. 2B and 3B), since the amount of the pressure difference is less than the preset threshold value.

The different pressure conditions for the correct and incorrect connection result from the different static pressures of the fluid-filled hose line segments. It can be seen that the arrangement of the ends of hose line segments 10b, 12a at different heights $\Delta h_1$ and $\Delta h_2$ in relation to the reference plane leads to different pressures. Two "fluid columns" are formed in line segments 10b, 12a.

Figure 4:
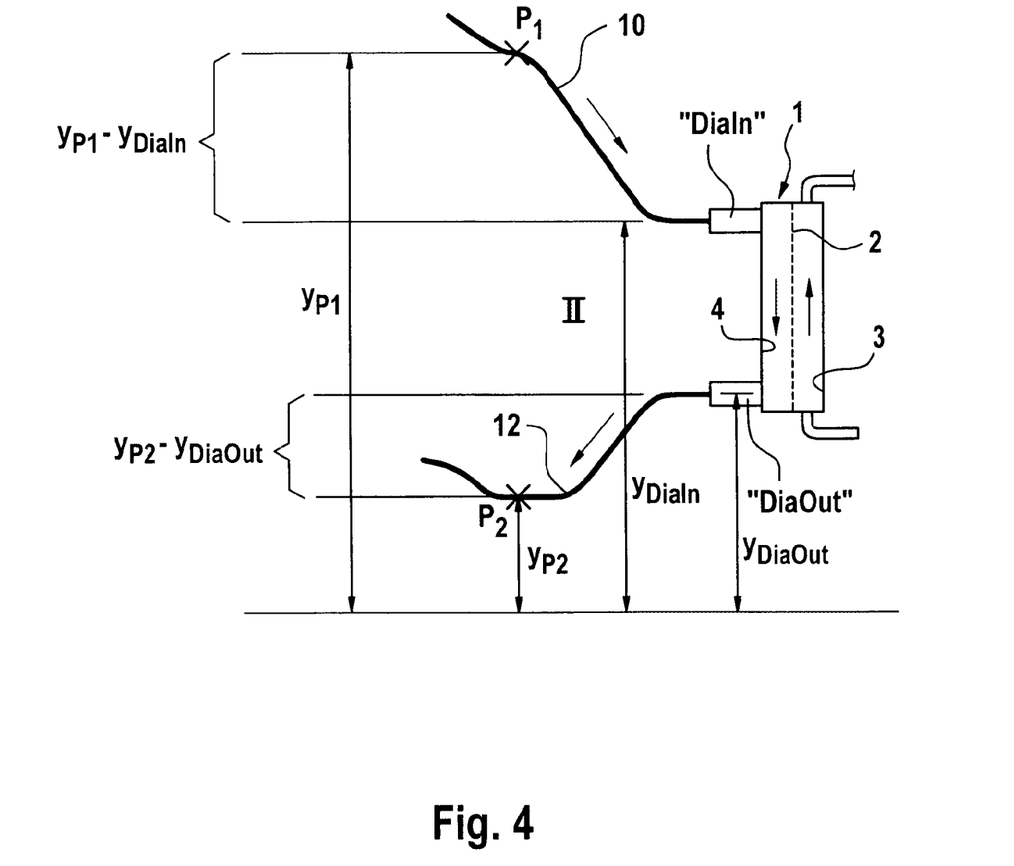
FIG. 4 shows, in a schematic representation, the line segments of the fluid system together with the measurement points of the pressure sensors.

FIG. 4 shows, for further illustration in a schematic representation, line segments 10, 12 of fluid system II leading to dialysing fluid chamber 4 of dialyser 1 and leading away from dialysing fluid chamber 4 of dialyser 1, together with the measurement points of first and second pressure sensors 42, 43 (FIG. 1), the first pressure sensor being arranged at measurement point P1 and the second sensor at measurement point P2. The two pressure sensors sit at the end of a completely filled, fixed-volume line closed at one end, said line being open to the surroundings at the other end. The hydrostatic pressure at pressure sensor P1 thus results from the height difference with respect to the dialyser connection, the same applying to the hydrostatic pressure at pressure sensor P2.

Let the heights of the pressure sensors and the dialyser connections be known:

Height of first pressure sensor: $y_{P1}$
Height of second pressure sensor: $y_{P2}$
Height of dialysate supply on dialyser: $y_{DiaIn}$
Height of dialysate return on dialyser: $y_{DiaOut}$ The following height difference then results for a connection according to the counter-flow principle:

$$\Delta y_{Counterflow} = (y_{P1} - Y_{DiaIn}) - (y_{P2} - Y_{DiaOut})$$

In the case of confusion of the connections, the following results:

$$\Delta y_{Coflow} = (y_{P1} - y_{DiaOut}) - (y_{P2} - y_{DiaIn})$$

The height difference between the correct and the incorrect filter connection is:

$$\Delta y = \Delta y_{Counterflow} - \Delta y_{Coflow}$$

$$\Delta y = [(y_{P1} - y_{DiaIn}) - (y_{P2} - y_{DiaOut})] - [(y_{P1} - y_{DiaOut}) - (y_{P2} - y_{DiaIn})]$$

$$= y_{P1} - y_{DiaIn} - y_{P2} + y_{DiaOut} - y_{P1} + y_{DiaOut} + y_{P2} - y_{DiaIn}$$

$$= -y_{DiaIn} + y_{DiaOut} + y_{DiaOut} - y_{DiaIn}$$

$$= 2(y_{DiaOut} - y_{DiaIn})$$

The position of the pressure sensors does not therefore play any role, only the distance between supply and discharge on the dialyser entering into the formula.

The height differences are proportional to the pressure:

$$\Delta y \sim \Delta p \rightarrow \Delta p_{connection} \sim 2(y_{DiaOut} - y_{DiaIn}) \quad \text{equation (1)}$$

In the present exemplary embodiment, the distance between the supply and discharge amounts to 25 cm. According to equation (1), a hydrostatic pressure difference between a correct and incorrect connection of the dialyser or filter of approx. 50 mbar therefore results.

In practice, the flow plan of the fluid system may be more complex. The hydraulic pressure at the respective pressure sensor results from the particular design of the fluid system on the one hand and the nature of the connection of the dialyser or filter on the other hand. However, since the fluid system always has the same influence on the hydrostatic pressure, a deviation of the pressure difference measured with the pressure sensors at measurement points P1 and P2 from the setpoint value can only be explained by an incorrect connection of the dialyser or filter. A prerequisite is that the state of the hydraulics at the time of the measurement is defined, this being the case immediately after the connection of the dialyser or filter (FIGS. 3A and 3B).

The pressure difference at measurement points P1 and P2 is ascertained within a preset time interval after the connection of the dialyser or filter to the line segments of the fluid system:

$$\Delta p_{mess} = P1 - P2$$

This value is compared with setpoint value $\Delta p_{system}$. Setpoint value $\Delta p_{system}$ is ascertained empirically for the blood treatment apparatus. It is possible to use only one empirically ascertained value for a plurality of blood treatment apparatuses of the same type. With value $\Delta p_{connection}$ calculated according to equation (1), the threshold is determined from which it is concluded that there is an incorrect connection of the dialyser or filter.

If the pressure difference between P1 and P2 is less than the setpoint value minus a preset tolerance, it is concluded that there is an incorrect connection of the dialyser or filter.

$$\Delta p_{mess} < \Delta p_{system} - f \cdot \Delta p_{connection}$$

Example:

$\Delta p_{system} = 50$ mbar (ascertained empirically)

$\Delta p_{connection} = 50$ mbar (on the basis of the minimum distance between the dialyser supply on the dialyser and the dialyser discharge on the dialyser)

$f = \frac{1}{2} \leftrightarrow \Delta p_{mess} < 25$ mbar

From a $\Delta p_{mess}$ less than 25 mbar, an incorrect connection of the dialyser is thus reported.

Central control unit 30 or computing and evaluation unit 40 comprise a memory 40A, in which the result of the check on the connection is stored. The correct or incorrect connection is thus recorded. The contents of the memory can be displayed on a display (not shown) of the blood treatment apparatus or can be read out.

In practice, only monitoring of the connections of blood treatment unit 1 to the line system of fluid system II is required. On the blood side, on the other hand, the risk of confusing the connections does not exist in practice. Purely theoretically, even if not readily practicable, it would however also be possible to provide the device according to the present invention for monitoring the connection of blood treatment unit 1 to hose lines 5, 7 of extracorporeal blood circuit I in order to monitor that the connections on the blood side are correct.

Figure 5:
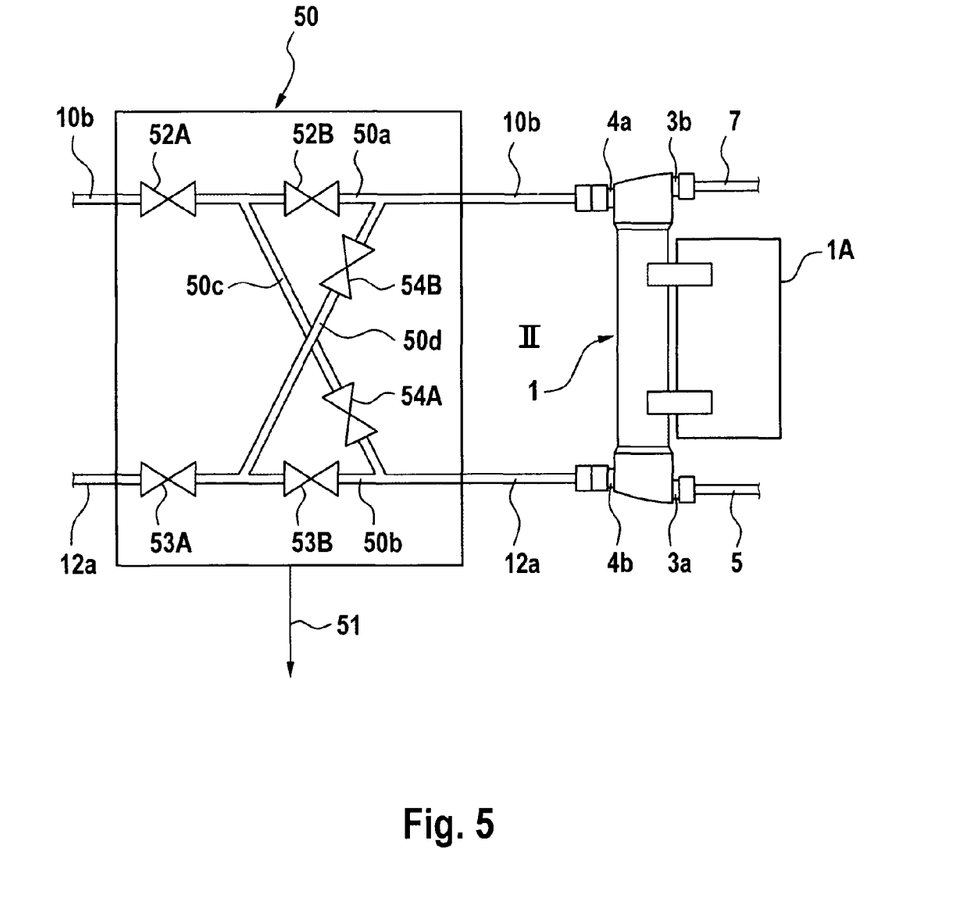
FIG. 5 shows a partial view of the fluid system of an alternative exemplary embodiment of the blood treatment apparatus in a simplified schematic representation, which comprises a device for reversing the flow direction.

FIG. 5 shows a part of fluid system II of an alternative exemplary embodiment of the blood treatment apparatus according to the present invention. The parts corresponding to one another are provided with the same reference numbers. The alternative exemplary embodiment differs from the exemplary embodiment described above in that a device 50 for reversing the flow direction, which is represented only schematically in FIG. 4, is incorporated into line segments 10b, 12a of dialysing fluid supply and discharge lines 10, 12. The device 50 for reversing the flow direction is connected via a data line 51 to computing and evaluation unit 40 of the monitoring device. When central control unit 30 of the blood treatment apparatus receives the control signal of computing and evaluation unit 40 which signals an incorrect connection of the blood treatment unit, central control unit 30 triggers the device 50 for reversing the flow direction, in such a way that the flow direction is reversed. In this exemplary embodiment, the Hansen couplings can in principle be connected arbitrarily, since the flow direction is automatically reversed after an incorrect connection is ascertained, so that the blood treatment unit is operated with a counter-flow.

The device 50 for reversing the flow direction comprise a first line segment 50a, which is incorporated into line segment 10b of dialysing fluid supply line 10, and a second line segment 50b, which is incorporated into line segment 12a of dialysing fluid discharge line 12. Two shut-off elements 52A, 52B and 53A, 53B, which can be actuated by central control unit 30, are incorporated respectively into first and second line segments 50a, 50b. Departing from the line segment lying between shut-off elements 52A, 52B is a first connection line 50c, which leads to the line segment between dialyser 1 and third shut-off element 53B. Leading away from the line segment lying between shut-off elements 53A, 53B is a second connection line 50d, which leads to the line segment between second shut-off element 52B and dialyser 1. A fifth shut-off element 54A is incorporated into first connection line 50c and a sixth shut-off element 54B is incorporated into second connection line 50d.

In the first place, fifth and sixth shut-off elements 54A and 54B are closed and other shut-off elements 52A, 52B and 53A, 53B are opened, so that the flow direction is not reversed. For the reversal of the flow direction, second and fourth shut-off elements 52B, 53B are closed and fifth and sixth shut-off elements 54A, 54B are opened. The opening and closing of the respective shut-off elements takes place automatically from control unit 30 depending on the result of the check on the connection of the blood treatment unit. In order to increase the reliability, a renewed check of the correct connection of blood treatment unit 1 can take place with the monitoring device after the reversal of the flow direction. In the present exemplary embodiment, shut-off elements 52A and 53A in the dialysing fluid supply and discharge lines 10 and 12 can also be dispensed with.

Figure 6A:
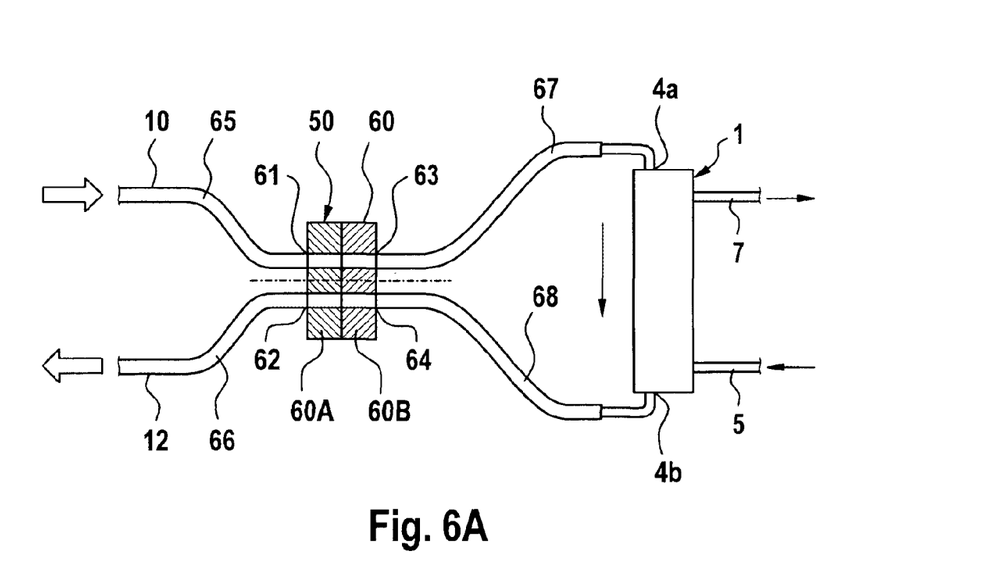
FIG. 6A shows a further alternative exemplary embodiment of the device for reversing the flow direction in a simplified schematic representation before the reversal of the flow direction.
Figure 6B:
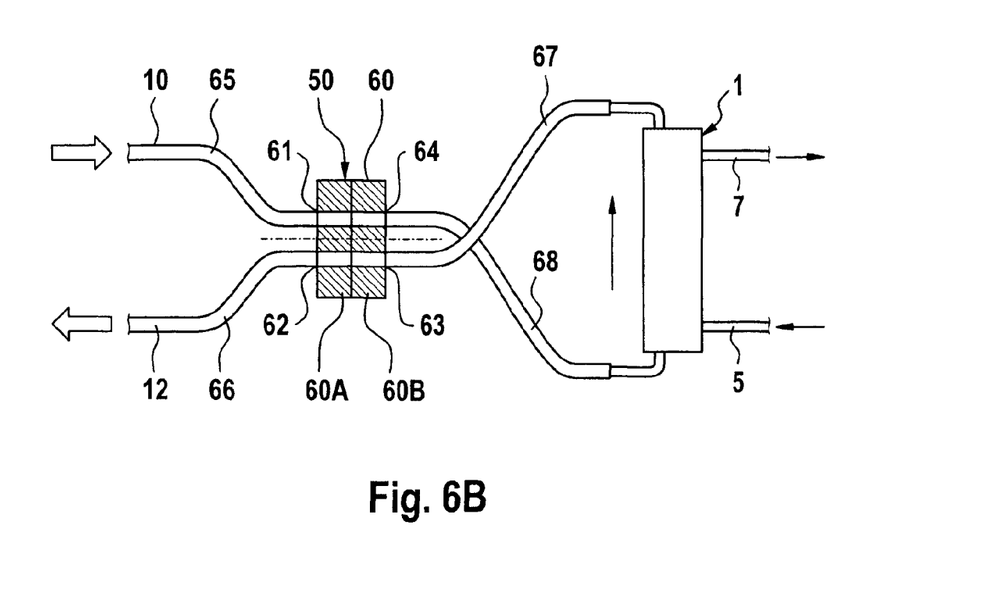
FIG. 6B shows a further alternative exemplary embodiment of the device for reversing the flow direction in a simplified schematic representation after reversal of the flow direction.

FIGS. 6A and 6B show a further alternative exemplary embodiment of the device for reversing the flow direction in a schematic representation, which differs from the exemplary embodiment of FIG. 5 in that, instead of individual shut-off elements in supply and discharge lines 10, 12, a common reversing valve is provided. The same reference numbers are again used for parts corresponding to one another. FIGS. 6A and 6B show device 50 for reversing the flow direction only in a schematic representation. Reversing valve 60 comprises a first and a second valve body 60A, 60B, which each have a first and a second connection 61, 62; 63, 64. First connection 61 of first valve body 60A is connected to a segment 65 of dialysing fluid line 10 that leads to the first valve body, whilst second connection 62 of first valve body 60A is connected to a segment 66 of dialysing fluid line 12 that leads away from first valve body 60A. First connection 63 of second valve body 60B is connected to a segment 67 of dialysing fluid line 10 leading away from the second valve body and leading to the one connection 4a of blood treatment unit 1, whilst second connection 64 of second valve body 60B is connected to a segment 68 of dialysing fluid line 12 leading away from the other connection 4b of blood treatment unit 1 and leading to the second valve body.

First and second valve bodies 60A, 60B can be rotated against one another in such a way that, in a first position (FIG. 6A), a flow connection is produced between first connections 61, 63 of first and second valve bodies 60A, 60B on the one hand and second connections 62, 64 of first and second valve bodies 60A, 60B on the other hand and, in a second position (FIG. 6B), a flow connection is produced between first connection 61 of first valve body 60A and second connection 64 of second valve body 60B and respectively second connection 62 of first valve body 60A and first connection 63 of second valve body 60B. The direction of the flow through the blood treatment unit, in particular the dialysing fluid chamber of the dialyser of filter, can thus be reversed. The rotation of valve bodies 60A, 60B takes place with a rotary drive (not shown), which is controlled by the control unit.

The device for reversing the flow direction is described in detail in U.S. Patent Application Publication No. 2006/0079827. In the present exemplary embodiment, however, the device for reversing the flow direction described in U.S. Patent Application Publication No. 2006/0079827 is used on the dialysing fluid side.

The invention claimed is:

1. A monitoring device for monitoring a pair of connections of a blood treatment unit to a fluid system of an extracorporeal blood treatment apparatus, wherein the blood treatment unit comprises an inlet for connection to the fluid system and an outlet for connection to the fluid system, the fluid system comprises a line system including a first line segment for connection to the inlet, and a second line segment for connection to the outlet, the monitoring device comprising:
    a first pressure sensor configured to measure a first static pressure in the first line segment;
    a second pressure sensor configured to measure a second static pressure in the second line segment; and
    an evaluation unit configured to determine a difference between the first static pressure measured and the second static pressure measured, said evaluation unit further being configured to, on a basis of the difference, determine whether a correct pair of connections or an incorrect pair of connections has been made between (1) the inlet and outlet, and (2) the first and second line segments,
    wherein the correct pair of connections has been made when the first line segment is connected to the inlet of the blood treatment unit and the second line segment is connected to the outlet of the blood treatment unit such that the blood treatment unit is operated with a counter-flow, and
    wherein the incorrect pair of connections has been made when the first line segment is connected to the outlet of the blood treatment unit and the second line segment is connected to the inlet of the blood treatment unit such that the blood treatment unit is not operated with a counter-flow.

2. The monitoring device according to claim 1, wherein the evaluation unit is configured such that the difference between the first static pressure measured and the second static pressure measured is compared with a preset threshold value, and the determination of the correct pair of connections or the incorrect pair of connections is made on a basis of the comparison of the difference with the preset threshold value.

3. The monitoring device according to claim 2, wherein the evaluation unit is configured to determine the incorrect pair of connections has been made if the difference between the first and second measured static pressures is less than the preset threshold value.

4. The monitoring device according to claim 1, further comprising:
    an alarm unit that emits at least one of an optical, acoustic, or tactile alarm when the evaluation unit determines the incorrect pair of connections has been made.

5. The device according to claim 2, wherein the evaluation unit is configured to determine that the correct pair of connections has been made if the difference between the first and second measured static pressures is greater than the preset threshold value.

6. The monitoring device according to claim 1, wherein the evaluation unit is configured such that the evaluation unit generates a control signal for intervention into machine control of the blood treatment apparatus when the evaluation unit determines that the incorrect pair of connections has been made.

7. An extracorporeal blood treatment apparatus, comprising:
    a central control unit;
    a fluid system, which comprises a line system with a first line segment which is connected to an inlet of a blood treatment unit and a second line segment which is connected to an outlet of the blood treatment unit; and
    the monitoring device according to claim 1 wherein the first pressure sensor is configured to measure static pressure in the first line segment and the second pressure sensor is configured to measure static pressure in the second line segment.

8. The apparatus according to claim 7, wherein the fluid system of the blood treatment apparatus comprises a first shut-off element for shutting off the first line segment and a second shut-off element for shutting off the second line segment of the fluid system, the first and second shut-off elements being controlled for opening and closing by the central control unit of the blood treatment apparatus.

9. The apparatus according to claim 8, wherein a first unit configured for measuring a first pressure in the first line segment is upstream of the first shut-off element and a second unit configured for measuring a second pressure in the second line segment is downstream of the second shut-off element.

10. The apparatus according to claim 9, wherein the central control unit of the blood treatment apparatus cooperates with the evaluation unit of the monitoring device such that, after the opening of the first and second shut-off elements, the first and second measured pressures of the first and second units configured for measuring the pressures in the first and second line segments are evaluated.

11. The apparatus according to claim 7, wherein the line system comprises a device configured for reversing a flow direction, which is constituted such that, in a first position, the first line segment leads to the inlet of the blood treatment unit and the second line segment leads to the outlet of the blood treatment unit and that, in a second position, the first line segment leads to the outlet of the blood treatment unit and the second line segment leads to the inlet of the blood treatment unit when the blood treatment unit is connected to the fluid system.

12. The apparatus according to claim 11, wherein the evaluation unit cooperates with the device configured for reversing the flow direction such that the evaluation unit activates the device configured for reversing the flow direction when the evaluation unit determines the incorrect pair of connections of the blood treatment unit to the fluid system.

13. The apparatus according to claim 7, wherein the central control unit of the blood treatment apparatus is constituted such that the central control unit prevents performance of blood treatment when the evaluation unit of the monitoring device generates a control signal for intervention into machine control.

14. A method for monitoring a pair of connections of a blood treatment unit to a fluid system of an extracorporeal blood treatment apparatus, the method comprising:
    providing an extracorporeal blood treatment apparatus according to claim 7;
    measuring pressure in at least one of the first line segment and the second line segment of the line system; and
    determining that there is a correct pair of connections or incorrect pair of connections of the blood treatment unit to the fluid system on a basis of the measured pressure in at least one of the first line segment and the second line segment.

15. The method according to claim 14, further comprising:
    measuring a first pressure in the first line segment of the line system and a second pressure in the second line segment of the line system; and
    comparing a difference between the first measured pressure and the second measured pressure with a preset threshold value;
    wherein a correct or incorrect pair of connections of the blood treatment unit to the fluid system is determined on a basis of the comparison of the difference between the first and second measured pressures with the threshold value.

16. The method according to claim 15, wherein an incorrect pair of connections of the blood treatment unit to the fluid system is determined if the difference between the first and second measured pressures is less than the preset threshold value.

17. The method according to claim 15, further comprising:
    calculating an amount of the difference between the first measured pressure and the second measured pressure, the amount of the difference being compared with the preset threshold value.

18. The method according to claim 14, further comprising:
    emitting at least one of an optical, acoustic and tactile alarm when an incorrect pair of connections of the blood treatment unit to the fluid system is determined.

19. The method according to claim 14, further comprising:
    carrying out an intervention into machine control of the blood treatment apparatus by preventing performance of blood treatment, when an incorrect pair of connections of the blood treatment unit to the fluid system is determined.

20. The method according to claim 14, further comprising:
    reversing a flow direction to the blood treatment unit when an incorrect pair of connections of the blood treatment unit to the fluid system is determined.

* * * * *